(12) United States Patent
Board et al.

(10) Patent No.: US 8,287,916 B2
(45) Date of Patent: Oct. 16, 2012

(54) MULTI-PART KIT SYSTEM FOR THE PREPARATION OF A DISINFECTANT OF THE PERACETIC ACID TYPE

(75) Inventors: Kelly Ann Board, Sudbury (GB); Mark Wallace Squire, Newmarket (GB)

(73) Assignee: E I du Pont de Nemours and Company, Wilmington, DE (US)

( * ) Notice: Subject to any disclaimer, the term of this patent is extended or adjusted under 35 U.S.C. 154(b) by 244 days.

(21) Appl. No.: 12/714,792

(22) Filed: Mar. 1, 2010

(65) Prior Publication Data

US 2010/0227000 A1 Sep. 9, 2010

Related U.S. Application Data

(60) Provisional application No. 61/157,747, filed on Mar. 5, 2009.

(51) Int. Cl.
*A01N 39/00* (2006.01)
(52) U.S. Cl. ........................................ 424/616; 424/613
(58) Field of Classification Search .................. 424/613, 424/616
See application file for complete search history.

(56) References Cited

U.S. PATENT DOCUMENTS

| | | | | |
|---|---|---|---|---|
| 4,477,438 A | * | 10/1984 | Willcockson et al. | 424/616 |
| 4,772,290 A | * | 9/1988 | Mitchell et al. | 8/107 |
| 5,021,182 A | * | 6/1991 | Jentsch | 510/306 |
| 2002/0182103 A1 | * | 12/2002 | Biering et al. | 422/28 |
| 2004/0022867 A1 | | 2/2004 | Tucker et al. | |
| 2005/0109981 A1 | | 5/2005 | Tucker et al. | |
| 2007/0031464 A1 | * | 2/2007 | Burban et al. | 424/405 |
| 2007/0249509 A1 | * | 10/2007 | Tucker | 510/110 |

FOREIGN PATENT DOCUMENTS

| | | |
|---|---|---|
| DE | 19651415 A1 | 6/1998 |
| WO | 03082014 A1 | 10/2003 |
| WO | 2008079170 A2 | 7/2008 |

OTHER PUBLICATIONS

Benzalkonium Chloride MSDS—accessed at www.sciencelab.com/msds.php?msdsld=9923038 on Jan. 20, 2012.*

Variquat 80MC CAS entry, Registry No. 68424-85-1, accessed on Jan. 19, 2012.*

* cited by examiner

*Primary Examiner* — James H. Alstrum-Acevedo

(57) ABSTRACT

A multi-part kit system comprising a solid part A which comprises at least one acetyl donor, a liquid part B in the form of an aqueous composition which comprises 3 to 35 wt. % of hydrogen peroxide and one or more parts C, wherein the solid part A and/or the part(s) C comprise at least one surfactant selected from the group consisting of anionic surfactants, amphoteric surfactants and nonionic surfactants, wherein the composition of the parts of the multi-part kit system is such, that directly after being mixed with each other and water in a specified ratio the pH of the mixture is in the range of 5.5 to 8.

18 Claims, No Drawings

MULTI-PART KIT SYSTEM FOR THE PREPARATION OF A DISINFECTANT OF THE PERACETIC ACID TYPE

CROSS-REFERENCE TO RELATED APPLICATIONS

This application claims the benefit of U.S. Provisional Application No. 61/157747 filed Mar. 5, 2009.

FIELD OF THE INVENTION

The invention relates to a multi-part kit system for the preparation of a disinfectant of the peracetic acid type (peracetic acid disinfectant) and the use thereof in a process for the preparation of a disinfectant of the peracetic acid type.

BACKGROUND OF THE INVENTION

Disinfectants of the peracetic acid type are well-known. They may be prepared by mixing acetic acid with hydrogen peroxide and letting the mixture react in aqueous medium to yield an aqueous equilibrium peracetic acid solution. However, such aqueous equilibrium peracetic acid solutions make high demands with regard to shipping and storage because of their oxidizing and corrosive properties and relative instability, which do not allow for ease of shipping in high-concentrate form.

An alternative is the in-situ generation of peracetic acid from a precursor, for example, tetraacetyl ethylene diamine (TAED) and a source of peroxide, for example, hydrogen peroxide itself and/or a hydrogen peroxide source, for example, inorganic per-salts, such as perborate, percarbonate, perphosphate, persulfate, and persilicate salts.

Examples 2 to 6 of US 2005/0109981 A1 disclose two-part kit systems for the preparation of disinfectants of the peracetic acid type. The two-part kit systems disclosed therein consist in each case of a part A comprising an acetyl donor and a part B comprising a hydrogen peroxide solution that may contain potassium acetate.

SUMMARY OF THE INVENTION

The present invention provides an easy-to-use multi-part kit system for the preparation of a disinfectant of the peracetic acid type which is distinguished by not only a long shelf life of its parts of, for example, 18 to 24 months and more, but also a short activation time even at low temperatures, as may prevail, for example, in a farm environment in particular in the cold time of the year. Peracetic acid disinfectants prepared from the multi-part kit system of the present invention are distinguished by good storage stability.

Accordingly, the present invention provides a multi-part kit system, for example, a two- or three-part kit system comprising a solid part A which comprises at least one acetyl donor, a liquid part B in the form of an aqueous composition which comprises 3 to 35 wt. % (weight-%), preferably 5 to 10 wt. % of hydrogen peroxide (hereinafter for brevity purposes also called "liquid part B") and, optionally, one or more parts C, wherein (a) the solid part A or the optional part(s) C or (b) the solid part A and the optional part(s) C, comprise at least one surfactant selected from the group consisting of anionic surfactants, amphoteric (zwitterionic) surfactants and nonionic surfactants, wherein the composition of the parts of the multi-part kit system is such, that directly after being mixed with each other and water in a specified ratio the pH of the mixture is in the range of 5.5 to 8.

DETAILED DESCRIPTION OF THE INVENTION

The term "multi-part kit system" is used in the description and the claims. It means a kit system comprised of several parts which are stored separate from each other until being used; i.e., until the parts are mixed to form the peracetic acid disinfectant.

The term "solid part A" is used in the description and the claims. It refers to the fact that part A of the multi-part kit system of the present invention is a solid, although it is possible that not all of its constituents are solid. The solid part A may be in the form of a flowable powder or it may take the form of pellets or tablets, for example. The solid nature of part A allows for its easy dosing when mixing it with the liquid part B, the optional part(s) C and water in the specified ratio to prepare the peracetic acid disinfectant.

The term "wherein the composition of the parts of the multi-part kit system is such, that directly after being mixed with each other and water in a specified ratio, the pH of the mixture is in the range of 5.5 to 8" is used in the description and the claims. It refers to the fact that, when the parts of the multi-part kit system have been mixed with each other and water in a specified ratio, an initial pH of the mixture; i.e., a pH measured directly after mixing, for example, within 5 to 10, in particular within 10 minutes after mixing, in the range of 5.5 to 8 is achieved. The pH measurement can be performed making use of a conventional pH meter.

The term "specified ratio" is used in the description and the claims. It means the mixing ratio to be applied when mixing the parts of the multi-part kit system and water. That is, there will be a specified ratio between part A and part B and water or between part A and part B and part(s) C and water. Typically, the specified ratio is recommended by the supplier of the multi-part kit system, to accommodate the particular concentrations of the components within the part A, part B and optional part(s) C.

In an embodiment, the present invention provides a multi-part kit system without any parts C; i.e., a two-part kit system consisting of (i) a solid part A comprising at least one acetyl donor, for example, 2 to 90 wt. % of at least one acetyl donor, and at least one surfactant selected from the group consisting of anionic surfactants, amphoteric surfactants and nonionic surfactants, for example, 1 to 30 wt. % of at least one surfactant selected from the group consisting of anionic surfactants, amphoteric surfactants and nonionic surfactants, and (ii) a liquid part B in the form of an aqueous composition comprising 3 to 35 wt. %, preferably 5 to 10 wt. % of hydrogen peroxide, wherein the composition of parts A and B is such, that directly after being mixed with each other and water in a specified ratio the pH of the mixture is in the range of 5.5 to 8.

It is preferred that the two-part kit system is supplied to the user in the form of two separate receptacles one of which containing the solid part A and the other containing the liquid part B, wherein the specified ratio between parts A and B and water not only ensures that the pH of the mixture of parts A and B and water directly after mixing is in the range of 5.5 to 8 but also corresponds to a molar ratio between the acetyl groups of the at least one acetyl donor in part A and the hydrogen peroxide in part B of 4:1 to 1:10, in particular 2:1 to 1:2. Therefore, in a preferred embodiment, the present invention provides a two-part kit system consisting of (i) a solid part A comprising 2 to 90 wt. % of at least one acetyl donor and 1 to 30 wt. % of at least one surfactant selected from the group consisting of anionic surfactants, amphoteric surfactants and nonionic surfactants and (ii) a liquid part B in the form of an aqueous composition comprising 3 to 35 wt. %, preferably 5 to 10 wt. % of hydrogen peroxide, wherein the composition of parts A and B is such, that directly after being mixed with each other and water in a specified ratio the pH of the mixture is in the range of 5.5 to 8, and wherein the specified ratio between parts A and B corresponds to a molar ratio between the acetyl groups of the at least one acetyl donor in solid part A and the hydrogen peroxide in liquid part B of 4:1 to 1:10, in particular 2:1 to 1:2.

The term "molar ratio between the acetyl groups of the at least one acetyl donor in solid part A and the hydrogen peroxide in liquid part B" is used in the description and the claims. To avoid misunderstandings, the molar ratio is calculated taking into account all acetyl groups of the at least one acetyl donor in solid part A, irrespective of whether all or only part of those acetyl groups are available for or do engage in an acetylating reaction in the course of which peracetic acid is formed.

As already mentioned, although part A of the two- or multi-part kit system of the present invention is solid, it may comprise liquid constituents, for example, in a total proportion of up to 20 wt. %. It is however preferred that the solid part A comprises only solid constituents.

The solid part A of the two-part kit system of the present invention comprises at least one acetyl donor, for example, 2 to 90 wt. %, particularly 30 to 60 wt. % of at least one acetyl donor, and at least one surfactant selected from the group consisting of anionic surfactants, amphoteric surfactants and nonionic surfactants, for example, 1 to 30 wt. %, particularly 1 to 15 wt. % of at least one surfactant selected from the group consisting of anionic surfactants, amphoteric surfactants and nonionic surfactants.

It is preferred that the at least one acetyl donor is a solid compound. Examples of acetyl donors include tetraacetyl ethylene diamine (TAED), acetyl salicylic acid, pentaacetylglucose, tetraacetylglycoluril, N-acetyl caprolactam, diacetin, triacetin, acetyl triethyl citrate and 1,5-diacetyl-2,4-dioxo-hexahydro-1,3,5-triazine. TAED is preferred as acetyl donor. In a preferred embodiment part A comprises 30 to 60 wt. % of TAED, wherein it is especially preferred that the TAED is the only acetyl donor.

It is preferred that the at least one surfactant is a solid compound or a solid material. For example, it may also take the form of a waxy compound or material or the form of a liquid compound or material which has been encapsulated with, for example, inorganic carriers, such as silica, zeolites, or organic agents, such as starch, cellulose, gum, lipids and proteins. The at least one surfactant is selected from the group consisting of anionic surfactants, amphoteric surfactants and nonionic surfactants. Examples of anionic surfactants include sodium alkyl sulfates and sodium alkyl benzene sulfonic acids. Examples of commercially available anionic surfactants that can be used in part A include Ufapol® TEP2 P from Unger Fabrikker AS, Hostapur® SAS 60 from Clariant, Ufaryl® DL 85 from Biachem Specialities Ltd, Marlon® ARL from The White Sea and Baltic Co. Ltd. and Marlon® AS3 from Surfachem Ltd. In case the multi-part or two-part kit system comprises one or more salts comprised of organic cations with at least one positively charged nitrogen atom, for example, quaternary ammonium salts, it is preferred not to use anionic surfactants in the parts of the kit system. Examples of amphoteric surfactants include betaine-, glycinate-, aminopropionate-, amphoacetate- and imidazoline-based amphoterics. Examples of commercially available amphoteric surfactants that can be used in part A include Ampholak® YCE and Ampholak® XCE both from Akzo Nobel, Amphoteric® SC from Tomah, Mackam® 2CY from McIntyre Group and Mirataine® D40 from Rhone-Poulenc. Nonionic surfactants are preferred. Nonionic surfactants are in particular ones comprising at least one polyoxyethylene and/or polyoxypropylene and/or polyoxyethylene/oxypropylene moiety. Preferred examples of such nonionic surfactants include polyethoxylated alcohols, in particular, polyethoxylated fatty alcohols. Examples of commercially available nonionic surfactants that can be used in part A include Rovol T500, from White Sea and Baltic Company Ltd., and Lutensol® AT 50 from BASF. It may happen that the commercially available surfactants are not pure active substance and they may contain water and/or organic solvents and/or other auxiliary substances; however, the corresponding wt. % specifications made in the description and the claims refer to active substance; i.e., surfactant as such.

Apart from the at least one acetyl donor and the at least one surfactant, the solid part A may comprise one or more of the following optional constituents: solid inorganic dispersants, solid water-soluble inorganic fillers, solid inorganic bases, biocidal compounds other than biocidal peroxide compounds and further additives.

The solid part A comprises 0 to 10 wt. %, preferably 1 to 5 wt. % of one or more solid inorganic dispersants. In case that part A is a powder, the inorganic dispersant may serve to aid flowability of such part A powder. Examples of solid inorganic dispersants include calcium phosphate and sodium phosphate and, in particular, silica. Silica is available as a fine powder from many suppliers, either as pyrogenic or as precipitated silica. Both types of silica may be used here.

The solid part A comprises 0 to 92 wt. %, preferably 40 to 69 wt. % of one or more solid water-soluble inorganic fillers. The water-soluble inorganic fillers are inert with regard to the other constituents of parts A and B and optionally present part(s) C; this is true even after the parts have been mixed with each other and water. Examples of water-soluble inorganic fillers include in particular sodium acetate, sodium sulfate, potassium sulfate and magnesium sulfate.

The solid part A comprises 0 to 20 wt. %, preferably 2 to 10 wt. % of one or more solid inorganic bases. Examples of such inorganic bases include sodium bicarbonate, potassium carbonate, sodium hydroxide, potassium hydroxide and, in particular, sodium carbonate.

The solid part A comprises 0 to 25 wt. %, preferably 5 to 10 wt. % of one or more biocidal compounds other than biocidal peroxide compounds, for example, biocidal phenol compounds and, in particular, biocidal compounds selected among salts comprised of organic cations with at least one positively charged nitrogen atom and counteranions selected from the group consisting of propionates, saccharinates, methosulfates and halide anions, in particular chloride or bromide. Examples of biocidal phenol compounds include 4-chloro-3-methyl-phenol and sodium salts thereof, 2-phenylphenol and sodium salts thereof, p-chloro-m-xylenol, o-benzyl-p-chlorophenol and dichlorophen. Examples of such commercially available biocidal phenol compounds that can be used in part A include Nipacide® PC BP, Nipacide® PCNa, Nipacide® OPP, Nipacide® SOPP, Nipacide® BCP from Clariant, Preventol® O Extra from Bayer and PCMX® from Thomas Swan & Co. Examples of salts comprising organic cations with at least one positively charged nitrogen atom are hydrochloride salts of poly(hexamethylenebiguanide) or of chlorhexidine but also quaternary ammonium salts, such as benzalkonium chlorides, dialkyldimethyl ammonium chlorides such as didecyldimethylammonium chloride and di(hydrogenated tallow)dimethyl ammonium chloride, coco(fractionated)benzyl dimethylammonium chloride, alkyltrimethyl ammonium chlorides and esterquats. Examples of such commercially available salts that can be used in part A include Barquat® CB50/80, Barquat® CT35, Barquat® DM50/80, Barquat® LB50, Barquat® MB50/80, Barquat® MS100, Barquat® BB50, Bardac® 22, Bardac® 2240, Bardac® 2270, and Bardac® 2270E from Lonza; Arquad® 16-29, Arquad® 16-50, Arquad® 2.10-80, Arquad® 2HT-75, Arquad® 2HT-75E, Arquad® 2HT-75PG, Arquad® MCB-50, Arquad® MCB-80, and Arquad® MCB-80(S) from Akzo Nobel Surfactants; Ammonyx® CETAC, BTC® series and Stepanquat® series from Stepan; and Empigen® BAC series from Huntsman. It may happen that the commercially available salts are not pure active substance and they may contain water and/or organic solvents and/or other auxiliary substances; however, the corresponding wt. % specifications made in the description and the claims refer to active substance; i.e., the biocidal compound(s) as such.

The solid part A may comprise one or more further additives in a total proportion of, for example, up to 5 wt. %. Examples of such further additives include buffers such as, for example, alkali phosphates; dyes and peroxide decomposition stabilizers such as transition metal sequestering (complexing, chelating) agents. Examples of transition metal sequestering agents comprise compounds having nitrogen and/or oxygen donors as ligands, such as dimethylglyoxime, triazacycloalkane compounds, especially 1,4,7-triazacyclononanes (TACNs) or dipyridylamine (DPA); carboxylic acid derivatives such as ethylenediamine-N,N,N',N'-tetraacetic acid (EDTA) and its alkali salts, diethylenetriamine-N,N,N',N',N''-pentaacetic acid (DTPA) and its alkali salts, nitrilo-2,2',2''-triacetic acid (NTA) and its alkali salts; phosphonic acid derivatives such as 1,2-diaminocyclohexyl tetra(methylene phosphonic acid) and its alkali salts, diethylene triamine penta(methylene phosphonic acid) and its alkali salts, ethylene diamine tetra(methylene phosphonic acid) and its alkali salts, polyphosphate compounds and their alkali salts.

A preferred solid part A of the two-part kit system of the present invention has a composition as follows:
30 to 60 wt. % of acetyl donor, preferably TAED,
1 to 15 wt. % of nonionic surfactant, preferably polyethoxylated alcohol,
0 to 5 wt. %, preferably 1 to 5 wt. % of solid inorganic dispersant, preferably silica,
0 to 69 wt. %, preferably 40 to 69 wt. % of water-soluble solid inorganic filler, preferably sodium acetate or sodium sulfate,
0 to 10 wt. % of solid inorganic base, preferably sodium carbonate,
0 to 25 wt. %, preferably 5 to 10 wt. % of quaternary ammonium chloride, and
0 to 5 wt. % of one or more further additives selected from the group consisting of buffers, dyes and peroxide decomposition stabilizers,
wherein the sum of the wt. % totals 100 wt. %.

An even more preferred solid part A of the two-part kit system of the present invention has a composition as follows:
30 to 60 wt. % TAED,
1 to 15 wt. % of polyethoxylated alcohol, preferably polyethoxylated fatty alcohol,
0 to 5 wt. %, preferably 1 to 5 wt. % of solid inorganic dispersant, preferably silica,
0 to 69 wt. %, preferably 40 to 69 wt. % of water-soluble solid inorganic filler, preferably sodium acetate or sodium sulfate,
0 to 10 wt. % of solid inorganic base, preferably sodium carbonate,
0 to 25 wt. %, preferably 5 to 10 wt. % of quaternary ammonium chloride, and
0 to 5 wt. % of one or more further additives selected from the group consisting of buffers, dyes and peroxide decomposition stabilizers,
wherein the sum of the wt. % totals 100 wt. %.

A particularly preferred solid part A of the two-part kit system of the present invention has a composition as follows:
30 to 60 wt. % TAED,
1 to 15 wt. % polyethoxylated alcohol, preferably polyethoxylated fatty alcohol,
1 to 5 wt. % silica,
40 to 68 wt. % of water-soluble solid inorganic filler, preferably sodium acetate or sodium sulfate,
0 to 10 wt. % of solid inorganic base, preferably sodium carbonate,
0 to 25 wt. %, preferably 5 to 10 wt. % of quaternary ammonium chloride, and
0 to 5 wt. % of one or more further additives selected from the group consisting of buffers, dyes and peroxide decomposition stabilizers,
wherein the sum of the wt. % totals 100 wt. %.

The solid part A may be prepared by mixing, in particular powder blending, all the required constituents. Although part A as the product resulting from such mixing operation is solid, it is possible that not all of the constituents of part A are solid themselves, as has already been mentioned. Apart from mixing operations the preparation of solid part A may also include grinding operations.

The liquid part B of the two- or multi-part kit system of the present invention is an aqueous composition, in particular an aqueous solution, comprising 3 to 35 wt. %, preferably 5 to 10 wt. % of hydrogen peroxide and having a pH value of 3.5 to 8, preferably of 6.5 to 7.5.

The liquid part B may be commercially available aqueous hydrogen peroxide of pH 3.5 or it can be prepared by adjusting the pH value of an aqueous solution of hydrogen peroxide to the desired value; i.e., to a pH value of above 3.5 to 8, preferably of 6.5 to 7.5, by adding an appropriate amount of at least one inorganic base and, optionally, by dilution to the desired hydrogen peroxide concentration with water, preferably deionized or distilled water. Adjustment of the pH value can be controlled making use of a conventional pH meter.

Aqueous solutions of hydrogen peroxide are commercially available; typically they comprise 15 to 50 wt. %, in general 15 to 35 wt. % of hydrogen peroxide and have an acidic pH value in the range of 1 to 3.5.

Examples of inorganic bases that can be used for the pH adjustment are alkali metal carbonates and alkali metal hydroxides such as lithium hydroxide, sodium hydroxide and potassium hydroxide. It is preferred to use aqueous solutions of the bases. It is preferred to use an alkali metal hydroxide. If a dilution to the desired hydrogen peroxide concentration with water is carried out, this can be performed prior to, during or after the pH adjustment.

Apart from hydrogen peroxide, water and inorganic base, the liquid part B may comprise at least one further additive in a total proportion of, for example, 0 to 15, preferably 0.05 to 5 wt. %. Examples include surfactants, in particular nonionic, amphoteric and cationic surfactants; hard water sequestrants; corrosion inhibitors; and, peroxide decomposition stabilizers such as transition metal sequestering agents. Examples of the latter have already been mentioned above.

A preferred liquid part B has a composition as follows:
3 to 35 wt. %, preferably 5 to 10 wt. % of hydrogen peroxide,
0.05 to 0.5 wt. % of alkali hydroxide,
0.005 to 1 wt. % of at least one transition metal sequestering agent, 0 to 10 wt. %, preferably 0 wt. %, of at least one further additive selected from the group consisting of surfactants, hard water sequestrants and corrosion inhibitors; and the wt. % proportion remaining is water to make 100 wt. %.

The preferred liquid part B may be prepared by mixing an aqueous solution of hydrogen peroxide with the remaining constituents, wherein the remaining constituents may take the form of aqueous preparations or aqueous solutions. When the aqueous solution of the hydrogen peroxide as well as the remaining constituents potentially or actually contain impurities in the form of traces of transition metal compounds, like transition metal salts, it is expedient to comprise at least one transition metal sequestering agent. Examples of the latter have already been mentioned above.

Preferred two-part kit systems consist of (i) a solid part A composed of 30 to 60 wt. % TAED, 1 to 15 wt. % of polyethoxylated alcohol, 0 to 5 wt. % of solid inorganic dispersant, 0 to 69 wt. % of water-soluble solid inorganic filler, 0 to 10 wt. % of solid inorganic base, 0 to 25 wt. % of quaternary ammonium chloride, and 0 to 5 wt. % of one or more further additives selected from the group consisting of buffers, dyes and peroxide decomposition stabilizers, wherein the sum of the wt. % totals 100 wt. %, and (ii) a liquid part B composed of 3 to 35 wt. % of hydrogen peroxide, 0.05 to 0.5 wt. % of alkali hydroxide, 0.005 to 1 wt. % of at least one transition metal sequestering agent, 0 to 10 wt. % of at least one further additive selected from the group consisting of surfactants, hard water sequestrants and corrosion inhibitors, wherein the wt. % proportion remaining is water to make 100 wt. %, and wherein the ratio between part A and B corresponds to a molar ratio between the acetyl groups of the TAED in part A and the hydrogen peroxide in part B of 4:1 to 1:10, in particular 2:1 to 1:2.

The two- or multi-part kit system of the present invention; i.e., in particular the solid part A and the liquid part B, can be shipped to the user where the individual parts can be stored separate from each other until being used for the preparation of the peracetic acid disinfectant. Both parts A and B have a long shelf life of, for example, 18 to 24 months and more, if stored in a dry and cool place, for example, not exceeding 25° C.

The present invention is also directed to a process for the preparation of a peracetic acid disinfectant by mixing all parts of the two- or multi-part kit system, in particular parts A and B of the two-part kit system, and water in the specified ratio.

The process of the present invention can be performed at the user's premises in particular. It is a considerable advantage that the mixing can successfully be performed even at low temperatures of, for example 5 to 10° C., temperatures as may prevail in a farm environment in winter, for example. In other words, even at such low temperatures the activation time is short, for example, 5 to 15 minutes until sufficient peracetic acid is formed for biocidal activity; i.e., until the peracetic acid disinfectant can be used to perform a disinfection task.

In case of the two-part kit system of the present invention it is preferred that the specified mixing ratio between parts A and B corresponds to a molar ratio between the acetyl groups of the at least one acetyl donor in solid part A and the hydrogen peroxide in liquid part B of 4:1 to 1:10, in particular 2:1 to 1:2. The preparation of the peracetic acid disinfectant can easily be performed by mixing parts A and B and water in the specified mixing ratio, for example, mixing parts A and B and water and, if necessary, diluting the aqueous mixture with water to the desired concentration.

It is possible to mix parts A and B into water to obtain the ready-to-use (RTU) peracetic acid disinfectant with the desired concentration dependent on the specific disinfection task to be performed; i.e., with the desired peracetic acid content in the range of, for example 0.04 to 0.7 wt. %.

Alternatively, parts A and B may be mixed together with a small amount of water to form a concentrate with a peracetic acid content of, for, example, 1 to 5 wt. %. Such concentrate may be diluted with water to form a ready-to-use peracetic acid disinfectant which can then be used for disinfection purposes. For example, the concentrate may be applied by proportioning equipment, which dilutes the concentrate to the required peracetic acid concentration. Examples of such proportioning equipment include chemical injectors and Dosatron® technologies.

Pure, deionized or distilled water may be used for mixing and dilution purposes. However, it is also possible to use tap water, but in that case it is recommended that at least part B comprises a peroxide decomposition stabilizer, in particular a transition metal sequestering agent.

The peracetic acid disinfectant prepared according to the process described hereinabove is reliably effective against a large number of germs, in particular pathogenic germs including bacteria, viruses, fungi, spores, yeasts and algae. It may be used for different disinfecting purposes, for example, in the food, milk, brewing or beverage industry; in the medical or surgery sector; in sanitary hygiene; and as already mentioned in particular in farming, for example, swine or poultry breeding, dairy farming, in laying batteries. It may be used in the disinfection of water-circulating systems, but in particular, is used by applying to surfaces for surface disinfection applications, for example, the disinfection of installations; equipment; pipework; containers; bottles; sanitary objects; work surfaces; furniture; walls; floors; ceilings or complete rooms or buildings; shoes and protective clothing of staff; transportation vehicles, especially the wheels thereof. For the purposes of surface disinfection the peracetic acid disinfectant may be applied by various application methods which are selected dependent on the kind of surface which is to be disinfected. Application methods include fogging (spraying, atomization), wiping, brushing, dipping and rinsing to name only the most common methods. In certain cases the application of the peracetic acid disinfectant may be followed by a water-rinse after the disinfectant has taken effect; however, generally this is not the case.

As already mentioned above, dependent on the specific disinfection task to be performed, the degree of dilution of the ready-to-use peracetic acid disinfectant will be selected at the lower, the upper or between the lower and the upper end of the concentration range of the peracetic acid.

For example, for routine disinfection the final ready-to-use peracetic acid disinfectant will typically comprise 0.05 to 0.2 wt. % of peracetic acid. Such ready-to-use peracetic acid disinfectant may be applied to a pre-cleaned surface, for example, at a rate of 300 ml/m$^2$ of surface area by conventional means, for example, using a knapsack sprayer or a pressure washer set.

For example, for equipment disinfection the final ready-to-use peracetic acid disinfectant will typically comprise 0.04 to 0.1 wt. % of peracetic acid. The equipment to be disinfected may be immersed in the ready-to-use peracetic acid disinfectant and may or may not be rinsed after removal.

For example, for disinfection tasks in a farm environment the final ready-to-use peracetic acid disinfectant will typically comprise 0.05 to 0.2 wt. % of peracetic acid. Examples of typical applications in a farm environment include vehicle washing, foot- and wheel-dips and surface disinfection, in particular walls, floors and ceilings of animal houses.

For example, for fogging disinfection the final ready-to-use peracetic acid disinfectant will typically comprise 0.5 to 0.7 wt. % of peracetic acid. Such ready-to-use peracetic acid disinfectant may be applied by conventional means, for example, using a thermal fogging machine at a rate of, for example, 2 ml/m³.

EXAMPLES

If not stated otherwise, % means weight-%.

Determination of $H_2O_2$ and PAAH (Peracetic Acid) in the Solutions Prepared in Examples 1 to 4:

2.0000 g±0.1 g of each solution prepared according to Examples 1 to 4 was accurately weighed into a clean 100 ml volumetric flask and the exact weight (Wt) recorded. Distilled water was used to dilute to volume and the solution was mixed well. 10.0 ml of the diluted solution was accurately pipetted and transferred to a clean 250 ml conical flask. 50 ml of distilled water was added, along with 3 ml of 20% Sulphuric Acid and 2 drops of Ferroin Indicator Solution. The solution was titrated with 0.1 M Cerium (IV) Sulphate solution until the solution turned to a pure blue color, recording the amount of titrant used (T1). The hydrogen peroxide content of the sample was calculated using the following formula:

$$\frac{T1 \times 0.1 \times 34 \times 100 \times 100}{1000 \times 2 \times 10 \times Wt} = \frac{T1 \times 1.7}{Wt} = \text{Hydrogen Peroxide \% } w/w$$

To this solution 1 g Potassium Iodide is added, and titrated with 0.01 M sodium thiosulphate back to the original orange color, recording the titre, T2 (ml).

$$\text{Peracetic Acid, \% } w/w = \frac{T2 \times 0.01}{1000} \times \frac{R}{2} \times \frac{100}{10} \times \frac{1}{Wt} \times 100 = \frac{T2 \times 0.38}{Wt}$$

Where: R=molecular mass of peracetic acid=76 and 2 moles Sodium Thiosulphate=1 mole peracetic acid Determination of $H_2O_2$ and PAAH in the RTU Solution Prepared in Example 5:

A 20 ml aliquot of the RTU solution was added to a clean 250 ml conical flask. 50 ml of distilled water was added, along with 3 ml of 20% sulphuric acid and 2 drops of Ferroin indicator solution. The solution was titrated with 0.1 M Cerium (IV) Sulphate solution until the solution turned to a pure blue color, recording the amount of titrant used (T1). The hydrogen peroxide content of the sample was calculated using the following formula:

$$\frac{0.1 \times T1 \times 34 \times 100}{1000 \times 2 \times \text{sample } vol} = \frac{T1 \times 0.17}{20} = \text{Hydrogen Peroxide \% } w/v$$

To this solution 1 g potassium iodide is added, and titrated with 0.1 M sodium thiosulphate back to the original orange color, recording the titre, T2 (ml).

$$\text{Peracetic Acid, \% } w/v = \frac{0.1 \times T2 \times 76 \times 100}{1000 \times 2 \times \text{sample } vol} = \frac{T2 \times 0.38}{20}$$

Determination of $H_2O_2$ and PAAH in the Concentrate Solution Prepared in Example 5:

1.0000 g±0.1 g of the solution prepared according to Example 5 was accurately weighed into a clean 250 ml conical flask containing 50 ml of distilled water, 3 ml of 20% sulphuric acid and 2 drops of Ferroin indicator solution. The solution was titrated with 0.1 M cerium (IV) sulphate solution until the solution turned to a pure blue color, recording the amount of titrant used (T1). The hydrogen peroxide content of the sample was calculated using the following formula:

$$\frac{T1 \times 0.1 \times 34 \times 100}{1000 \times 2 \times Wt} = \frac{T1 \times 1.7}{Wt} = \text{Hydrogen Peroxide \% } w/w$$

To this solution 1 g Potassium Iodide is added, and titrated with 0.1 M sodium thiosulphate back to the original orange color, recording the titre, T2 (ml).

$$\text{Peracetic Acid, \% } w/w = \frac{0.1 \times T2 \times 76 \times 100}{1000 \times 2 \times Wt} = \frac{T2 \times 0.38}{Wt}$$

General Procedure:

The two-part systems of Examples 1 to 5 were prepared by weighing out Parts A and B into separate glass beakers. The beakers were then placed in a 10° C. water bath. When the temperature of the contents of both beakers had reached 10° C., the beaker containing part B was poured into the beaker containing part A. The pH of the solution after mixing was recorded.

Comparative Example 1

Theoretical Peracetic Acid Yield: 1.73%

| Part A (organic components) | |
|---|---|
| Reagent | Quantity/g |
| Barquat ® MB 80 | 4 |
| Adogen ® 477 | 2 |
| Propylene Glycol | 20 |
| 1-Dodecanol | 0.8 |
| Diethylene Glycol Monobutyl Ether | 1.6 |
| 1,3-Butanediol | 1 |
| Polyethoxylated Glycerine | 8 |
| Diacetin | 16 |

| Part B | |
|---|---|
| Reagent | Quantity/g |
| 8% $H_2O_2$ | 100 |
| Sodium Acetate | 30 |
| Deionized Water | 24.6 |

The pH of the solution after mixing at 10° C. was measured to be 7.59. The peracetic acid levels formed in the solution after mixing were calculated by titration and shown below:

| Time | Weight | T1 | % $H_2O_2$ | T2 | % PAAH | pH |
|---|---|---|---|---|---|---|
| 5 mins | | | | | | |
| 10 mins | 2.0382 | 4.72 | 3.94 | — | 0.00 | 7.14 |
| 20 mins | 2.0797 | 4.88 | 3.99 | — | 0.00 | 7.11 |
| 30 mins | 2.1403 | 5.01 | 3.98 | — | 0.00 | 7.07 |
| 40 mins | 2.0019 | 4.72 | 4.01 | — | 0.00 | 7.03 |

Comparative Example 2

Theoretical Peracetic Acid Yield: 3.32%

| Part A | |
|---|---|
| Reagent | Quantity/g |
| Barquat ® MB 80 | 4 |
| Propylene Glycol | 36 |
| Diacetin | 16 |

| Part B | |
|---|---|
| Reagent | Quantity/g |
| 8% $H_2O_2$ | 100 |
| Sodium Acetate | 40 |
| Deionized Water | 12 |

The pH of the solution after mixing at 10° C. was measured to be 7.41. The peracetic acid levels formed in the solution after mixing were calculated by titration and shown below:

| Time | Weight (g) | T1 (ml) | % $H_2O_2$ | T2 (ml) | % PAAH | pH |
|---|---|---|---|---|---|---|
| 5 mins | | | | | | |
| 10 mins | 2.0238 | 4.82 | 4.05 | 0.2 | 0.04 | 7.46 |
| 20 mins | 2.0309 | 4.71 | 3.94 | 0.32 | 0.06 | — |
| 30 mins | 2.0293 | 4.68 | 3.92 | 0.16 | 0.03 | — |

Comparative Example 3

Theoretical Peracetic Acid Yield: 3.32%

| Part A | |
|---|---|
| Reagent | Quantity/g |
| Barquat ® MB 80 | 4 |
| Adogen ® 477 | 2 |
| Propylene Glycol | 20 |
| 1-Dodecanol | 0.8 |
| Diethylene Glycol Monobutyl Ether | 1.6 |
| 1,3-Butanediol | 1 |
| Polyethoxylated Glycerine | 8 |
| Diacetin | 16 |
| Triethanolamine | 6 |

| Part B | |
|---|---|
| Reagent | Quantity/g |
| 8% $H_2O_2$ | 100 |
| Deionized Water | 48.6 |

The pH of the solution after mixing at 10° C. was measured to be 9.17. The peracetic acid levels formed in the solution after mixing were calculated by titration and shown below:

| Time | Weight (g) | T1 (ml) | % $H_2O_2$ | T2 (ml) | % PAAH | pH |
|---|---|---|---|---|---|---|
| 5 mins | 2.0276 | 4.76 | 3.99 | — | 0.00 | 8.52 |
| 10 mins | 2.0483 | 4.95 | 4.11 | — | 0.00 | 7.06 |
| 20 mins | 2.0481 | 4.68 | 3.88 | 0.18 | 0.03 | 8.3 |
| 30 mins | 2.0195 | 4.79 | 4.03 | 0.21 | 0.04 | 8.02 |
| 1 hr | 2.022 | 4.48 | 3.77 | 0.38 | 0.07 | 7.73 |

Comparative Example 4

Theoretical Peracetic acid Yield: 3.28%

| Part A | |
|---|---|
| Reagent | Quantity/g |
| Barquat ® MB 80 | 4 |
| Triethanolamine | 6 |
| Propylene Glycol | 36 |
| Diacetin | 16 |

| Part B | |
|---|---|
| Reagent | Quantity/g |
| 8% $H_2O_2$ | 100 |
| Deionized Water | 48.6 |

The pH of the solution after mixing at 10° C. was measured to be 8.52. The peracetic acid levels formed in the solution after mixing were calculated by titration and shown below:

| Time | Weight (g) | T1 (ml) | % $H_2O_2$ | T2 (ml) | % PAAH | pH |
|---|---|---|---|---|---|---|
| 5 mins | 2.0358 | 4.43 | 3.70 | — | 0.00 | 8.47 |
| 10 mins | 2.0388 | 4.37 | 3.64 | 0.38 | 0.07 | |
| 20 mins | 2.0596 | 4.79 | 3.95 | 0.22 | 0.04 | 8.07 |
| 30 mins | 2.0265 | 4.37 | 3.67 | 0.34 | 0.06 | 7.82 |

Given the large amount of hydrogen peroxide and the small amount of peracetic acid measured in the solutions of Examples 1 to 4 it is difficult to obtain a precise measure of peracetic acid concentration, however the peracetic acid generated by these examples at 10° C. has been found to be significantly below 0.1% peracetic acid.

Example 5

According to the Invention; Theoretical Peracetic Acid Yield in Case of the RTU Solution 0.15%, in Case of the Concentrate Solution 3.80%

| Part A | |
|---|---|
| Reagent | Quantity/g |
| TAED | 4 |
| Rovol ® T500 | 0.5 |
| Sodium carbonate | 0.65 |
| Barquat ® MS-100 | 1 |
| Cabosil ® M5 | 0.1 |
| Sodium Sulphate | 3.75 |

| Part B | |
|---|---|
| Reagent | Quantity/g |
| 7.5% $H_2O_2$ solution, adjusted to pH 7.0 by addition of NaOH | 20 |
| Water (RTU/concentrate) | 1740/40 |

The peracetic acid formed by the RTU solution is given below:

| Time | T1 (ml) | % $H_2O_2$ | T2 (ml) | % PAAH | pH |
|---|---|---|---|---|---|
| 5 mins | 8.41 | 0.071 | 2.75 | 0.052 | 8.16 |
| 10 mins | 7.86 | 0.067 | 3.58 | 0.068 | 8.00 |
| 15 mins | 7.24 | 0.062 | 3.55 | 0.067 | 7.91 |
| 20 mins | 6.97 | 0.059 | 3.43 | 0.065 | 7.84 |
| 30 mins | 6.78 | 0.058 | 3.68 | 0.070 | 7.73 |
| 40 mins | 6.43 | 0.055 | 4.20 | 0.080 | 7.69 |
| 1 hr | 6.00 | 0.051 | 4.88 | 0.093 | 7.56 |

The peracetic acid formed by the concentrate solution is given below:

| Time | Weight (g) | T1 (ml) | % $H_2O_2$ | T2 (ml) | % PAAH |
|---|---|---|---|---|---|
| 5 mins | 1.0072 | 9.73 | 1.64 | 4.71 | 1.78 |
| 10 mins | 1.0615 | 9.56 | 1.53 | 4.96 | 1.78 |
| 15 mins | 1.0126 | 8.93 | 1.50 | 4.80 | 1.80 |
| 20 mins | 0.9898 | 8.4 | 1.44 | 4.88 | 1.87 |
| 30 mins | 1.0288 | 8.22 | 1.35 | 5.42 | 2.00 |
| 1 hr | 1.0200 | 7.24 | 1.21 | 6.32 | 2.35 |

From the above it can be seen that the $H_2O_2$ content of the Example 5 solutions reduces with time signifying that it is reacting with the acetyl donor to generate peracetic acid. In the comparative examples 1 to 4 on the other hand, the $H_2O_2$ content of the solution remains fairly constant.

The table below compares the theoretical and experimental peracetic acid yields for examples 1 to 5. The theoretical yields have been compared to the calculated experimental yields obtained after 30 minutes of reaction at 10° C.

| Example | Theoretical max. PAAH concentration/% | Experimental PAAH concentration (30 mins)/% | % Yield |
|---|---|---|---|
| 1 | 1.73 | 0 | 0% |
| 2 | 3.32 | 0.03 | 0.90% |
| 3 | 3.32 | 0.04 | 1.20% |
| 4 | 3.28 | 0.06 | 1.83% |
| 5 (RTU) | 0.15 | 0.07 | 46.67% |
| 5 (concentrate) | 3.80 | 2.00 | 52.56% |

For Example 5, after 30 minutes of mixing 46.7% and 52.6% yields of peracetic acid are observed. This figure is also supported by the rate of depletion of hydrogen peroxide $H_2O_2$ in the mixture. At the start of the reaction, the $H_2O_2$ content of the Example 5 solutions were 0.09% for RTU and 1.64% for the concentrate. However, after 30 minutes of mixing, the $H_2O_2$ content had significantly reduced to 0.058% and 1.35%, respectively.

What is claimed is:

1. A multi-part kit system comprising a solid part A which comprises at least one acetyl donor, a liquid part B in the form of an aqueous composition which comprises 3 to 35 wt. % of hydrogen peroxide and one or more parts C, wherein the solid part A or the part(s) C or the solid part A and the part(s) C comprise at least one surfactant selected from the group consisting of anionic surfactants, amphoteric surfactants and nonionic surfactants, wherein the composition of the parts of the multi-part kit system is such, that directly after being mixed with each other and water in a specified ratio the pH of the mixture is in the range of 5.5 to 8.

2. A two-part kit system consisting of a solid part A which comprises at least one acetyl donor and at least one surfactant selected from the group consisting of anionic surfactants, amphoteric surfactants and nonionic surfactants and a liquid part B in the form of an aqueous composition which comprises 3 to 35 wt. % of hydrogen peroxide, wherein the composition of parts A and B is such, that directly after being mixed with each other and water in a specified ratio the pH of the mixture is in the range of 5.5 to 8.

3. The multi-part kit system of claim 1 or the two-part kit system of claim 2 wherein the solid part A is a flowable powder or takes the form of pellets or tablets.

4. The multi-part kit system of claim 1 or the two-part kit system of claim 2 wherein the solid part A comprises only solid constituents.

5. The two-part kit system of claim 2 wherein the solid part A comprises at least one constituent selected from the group consisting of solid inorganic dispersants, solid water-soluble inorganic fillers, solid inorganic bases, biocidal compounds other than biocidal peroxide compounds and further additives selected from the group consisting of buffers, dyes and peroxide decomposition stabilizers.

6. The two-part kit system of claim 2 wherein the specified ratio between parts A and B corresponds to a molar ratio between the acetyl groups of the at least one acetyl donor in solid part A and the hydrogen peroxide in liquid part B of 4:1 to 1:10.

7. The two-part kit system of claim 6 wherein the solid part A comprises 2 to 90 wt. % of the at least one acetyl donor and 1 to 30 wt. % of the at least one surfactant.

8. The two-part kit system of claim 6 wherein the solid part A comprises 30 to 60 wt. % of the at least one acetyl donor and 1 to 15 wt. % of the at least one surfactant.

9. The two-part kit system of claim 8 wherein the solid part A has the following composition:
   30 to 60 wt. % tetraacetyl ethylene diamine (TAED),
   1 to 15 wt. % polyethoxylated alcohol surfactant,
   0 to 5 wt. % of solid inorganic dispersant,
   0 to 69 wt. % of water-soluble solid inorganic filler,
   0 to 10 wt. % of solid inorganic base,
   0 to 25 wt. % of quaternary ammonium chloride, and
   0 to 5 wt. % of one or more further additives selected from the group consisting of buffers, dyes and peroxide decomposition stabilizers,
   wherein the sum of the wt. % totals 100 wt. %.

10. The multi-part kit system of claim 1 or the two-part kit system of claim 2 wherein the liquid part B has a pH value of 3.5 to 8.

11. The multi-part kit system of claim 1 or the two-part kit system of claim 2 wherein the liquid part B is composed of 3 to 35 wt. % of hydrogen peroxide, 0.05 to 0.5 wt. % of alkali hydroxide, 0.005 to 1 wt. % of at least one transition metal sequestering agent, 0 to 10 wt. % of at least one further additive selected from the group consisting of surfactants, hard water sequestrants and corrosion inhibitors; and the wt. % proportion remaining is water to make 100 wt. %.

12. A process for the preparation of a peracetic acid disinfectant comprising (i) mixing all parts of the multi-part kit system of claim 1 and water in the specified mixing ratio or (ii) mixing parts A and B of the two-part kit system of claim 2 and water in the specified mixing ratio.

13. The process of claim 12, wherein the mixing is performed at temperatures of 5 to 10° C.

14. The process of claim 12 wherein the preparation of the peracetic acid disinfectant is performed 5 to 15 minutes prior to use by applying to a surface for a surface disinfection application.

15. The process of claim 13 wherein the preparation of the peracetic acid disinfectant is performed 5 to 15 minutes prior to use by applying to a surface for a surface disinfection application.

16. The process of claim 14 wherein applying to a surface is performed by fogging, wiping, brushing, dipping, or rinsing.

17. The process of claim 14 wherein applying to a surface is performed with a knapsack spray or a pressure washer set.

18. The process of claim 14 wherein equipment is disinfected by immersing the equipment in the peracetic acid disinfectant.

* * * * *